US00PP25775P3

(12) United States Plant Patent
Schoone

(10) Patent No.: US PP25,775 P3
(45) Date of Patent: Aug. 4, 2015

(54) ***PHALAENOPSIS* ORCHID PLANT NAMED 'ZIPPITY'**

(50) Latin Name: *Phalaenopsis hybrida*
Varietal Denomination: Zippity

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 152 days.

(21) Appl. No.: 13/986,293

(22) Filed: Apr. 19, 2013

(65) Prior Publication Data

US 2013/0291250 P1 Oct. 31, 2013

Related U.S. Application Data

(60) Provisional application No. 61/637,992, filed on Apr. 25, 2012.

(30) Foreign Application Priority Data

Apr. 26, 2012 (NL) ..... OPS901

(51) Int. Cl.
*A01H 5/00* (2006.01)
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Zippity' particularly characterized by flowers which are white with some yellow in the labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Zippity'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Zippity'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Zippity' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Zippity' originated from a cross made by the inventor in 1999 in Strengweg, Heemskerk, The Netherlands. The female or seed parent is the *Phalaenopsis* cultivar designated 'Promis', unpatented. The male or pollen parent is the *Phalaenopsis* cultivar designated '(amabilis× White Castle×Moon World)', unpatented. The new *Phalaenopsis* 'Zippity' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture (mericloning) was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Zippity', which in combination distinguish this *Phalaenopsis* as a new and distinct cultivar:

1. flowers which are white with some yellow in the labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Zippity', the size of the flowers of the female parent 'Promis' is about 9 cm high and the size of the flowers of the male parent 'amabilis× White Castle×Moon World' is about 11 cm, whereas the size of the flowers of 'Zippity' is about 10 cm.

Presently, the commercial cultivar of *Phalaenopsis* orchid to which 'Zippity' can be meaningfully compared is 'Zola' (U.S. Plant patent application Ser. No. 13/986,341). The flower of Zippity is a little larger and the color of the labellum (next to the main color white) differs. Zippity has green/yellow in the labellum with a little orange and on the lateral lobes some red/purple stripes whereas 'Zola' has yellow/green with grey/orange which is more visible and on the lateral lobes some purple stripes. Also differs the shape of the labellum and the size of the cirrhi.

BRIEF DESCRIPTION OF THE PHOTOGRAPHS

The accompanying photographs illustrate the overall appearance of the new *Phalaenopsis* 'Zippity' showing the colors as true as is reasonably possible with colored reproductions of this type. Colors in the photographs may differ slightly from the color values cited in the detailed botanical description, which accurately describe the color of 'Zippity'.

DETAILED BOTANICAL DESCRIPTION

Figure 1:
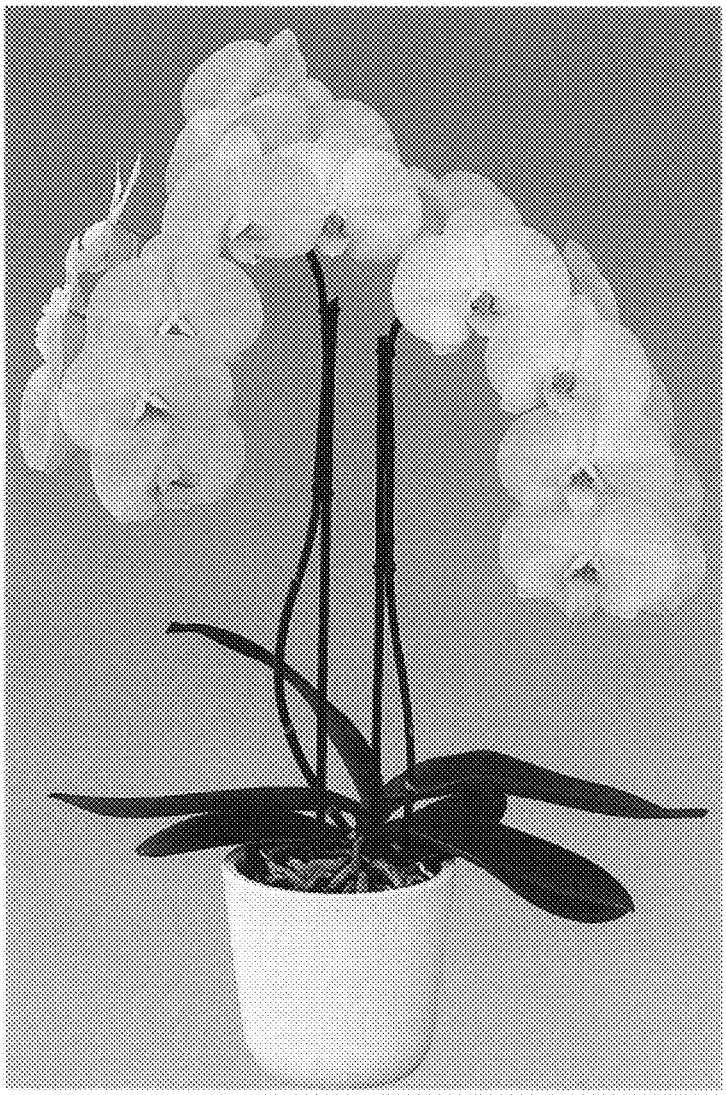
FIG. 1 shows a side view perspective of a typical flowering plant of 'Zippity' in a 12 cm pot, at 16 months of age.

The new *Phalaenopsis* cultivar 'Zippity' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Zippity' as grown in a greenhouse in Strengweg, Heemskerk, The Netherlands, under conditions which closely approximate those generally used in commercial practice. Initially, the ideal temperature to grow plants of 'Zippity' is 27° C. during the day and at night. Then, during the flowering phase of 'Zippity', the ideal growing temperature is 20-22° C. during the day and 18° C. at night. Light levels for growing 'Zippity' are a minimum of 5,000 lux and a maximum of 10,000 lux. A balanced fertilizer with level of 200 ppm N, 87 ppm P, 168 ppm K is applied. Duration of growth of 'Zippity' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Zippity' plants described is 12 months after potting.

Classification:

*Botanical.—Phalaenopsis hybrida.*

Parentage:

*Female or seed parent.—Phalaenopsis* cultivar designated 'Promis', unpatented.

*Male or pollen parent.—Phalaenopsis* cultivar designated '(amabilis×White Castle×Moon World)', unpatented.

Propagation:

*Type.*—Tissue culture.

*Rooting habit and description.*—Fleshy; approximately 3 mm-7 mm wide and green in color (RHS 137B); freely branching. It takes 12 weeks for plants growing in tissue culture to initiate roots.

Plant:

*Size at maturity.*—Height: about 57 cm. Spread: about 50 cm.

*Growth habit.*—Standard; dark-green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture (upper & underside).*—Smooth and leathery.

*Pubescence.*—None.

*Mature leaf length.*—About 13 to 22 cm.

*Mature leaf width.*—About 63 to 84 mm.

*Mature leaf thickness.*—About 1.5 mm.

*Mature leaf color.*—Upper side: green (RHS N137C); edges are lighter (RHS 143C). Under side: green (RHS 137C), edges are RHS 137A.

*Leaf base.*—Acute.

*Margin.*—Entire.

*Venation.*—Pattern: parallel. Color of midvein: upper side: green (RHS 137B). under side: red/purple (RHS 137C).

Inflorescence description:

*Appearance.*—Upright to slightly pendant, racemose inflorescence with bilaterally symmetrical flowers that open in succession beginning with the lowermost flower.

*Raceme.*—Quantity per plant: about 1 to 2. Number of flowers per raceme: about 6 to 10. Length: about 58 to 70 cm.

*Peduncle.*—Diameter: about 5 to 6 mm. Strength: strong. Aspect: upright. Texture: glabrous and smooth. Color: green (RHS 137A) with some RHS 137D.

*Buds.*—Height (from base to tip): about 25 mm. Diameter (at midpoint): about 20 mm. Shape: egg-shaped. Color: Main color is RHS 145B with a haze of red/purple (RHS 71A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
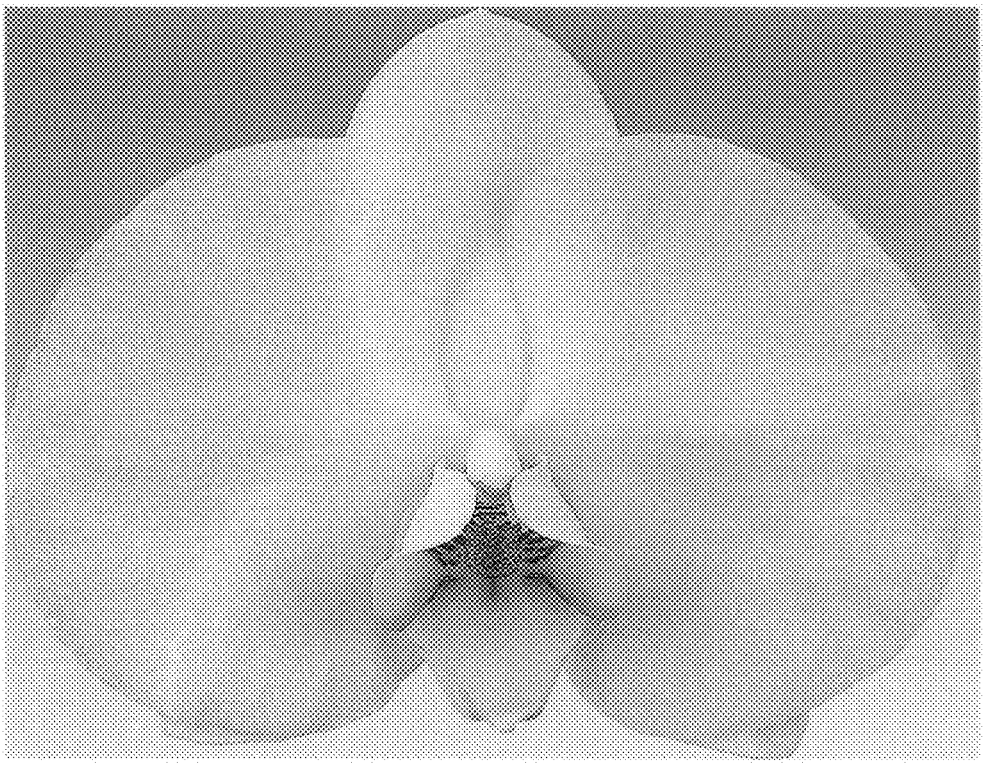
FIG. 2 shows a close-up view of a typical flower of 'Zippity'.
Figure 3:
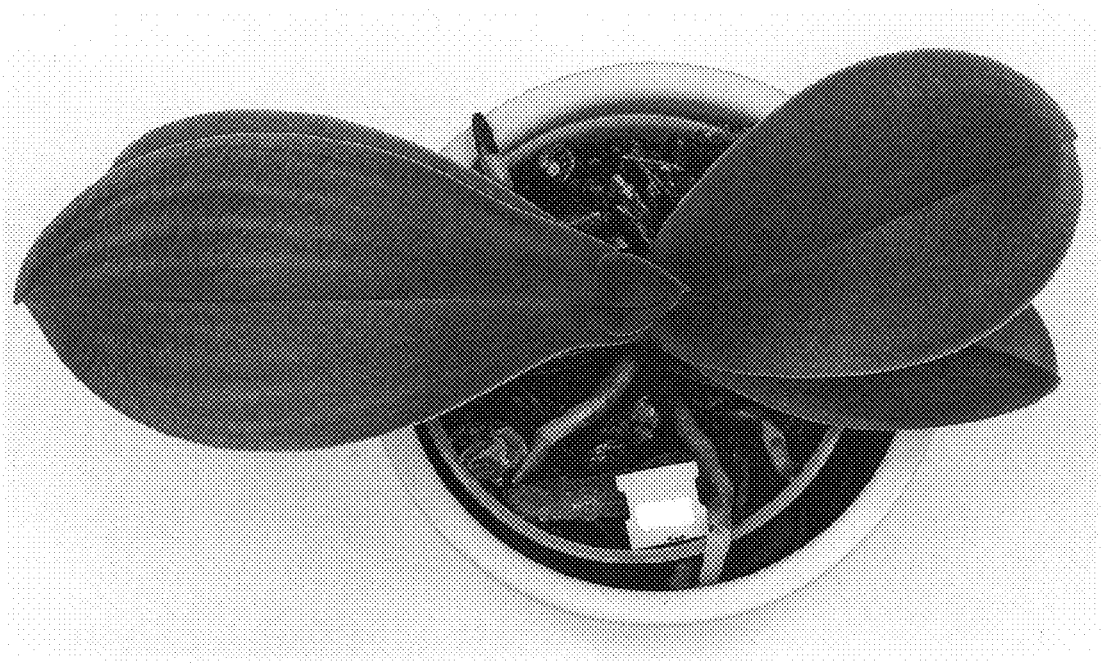
FIG. 3 shows a close-up view of the typical leaves of 'Zippity'.

*Flower*.—Rate of opening: Flowers fully opened about 2 to 3 days after petal and sepal separation. Orientation at opening: slanted upward and outward. Shape: Typical shape of *Phalaenopsis* orchid; see FIG. 2. Size (of single bloom): Height: about 65 mm to 85 mm. Diameter: about 70 mm to 105 mm. Quantity and arrangement: Three petals and three sepals that are trimerous, overlapping and arranged in 2 whorls. Petals are more pronounced than sepals.

*Petals*.—Arrangement: Inner whorl comprises 3 petals: 2 lateral petals and a labellum. 2 lateral petals: Overall shape: broadly ovate and weakly cupped. Apex: oval. Margin: entire and weakly undulate. Base: broadly ovate. Length: about 58 mm. Width: about 45 mm. Texture: Upper surface: smooth and satiny. Under surface: smooth and satiny. Color (when fully opened): upper side: white (RHS NN155C). Under side: white (RHS NN155C) with a light violet line (RHS 84C). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: lateral lobes: oval. Midlobe: round corners. Length: about 23 mm. Width (not flattened): about 26 mm. Depth of tube created by lateral lobes of labellum: about 17 mm. Texture: Upper and under surface: smooth and satiny. Color (when fully opened): Midlobe: upper surface: main color is white (RHS NN155C) with at the base and in the corners some green/yellow (RHS 1 B). Edges, stripe in the center and at the base some orange (RHS 26A). Under surface: main color is white (RHS NN155C) with some green/yellow in the corners (RHS 1B). Edges are orange (RHS 26A). At the base a little purple (RHS N81C). Lateral lobes: upper surface: main color is white (RHS NN155C), at the bottom some yellow (RHS 2B and RHS 1B). At the base some purple stripes (RHS N81A), bottom edges are orange/red (RHS N34C). Under surface: main color is white (RHS NN155C) with green/yellow (RHS 1 B). Also some purple/violet (RHS N81C) and edges are orange/red (RHS N34C). Cirrhi: long (about 19 mm) and curly with a point in between; color: white (RHS NN155C). Pestle (Callosities): Length: about 9 mm. Width (not flattened): about 6 mm. Color: Sides are white (RHS NN155C), edges, top and inside is yellow (RHS 2A) with orange/red spots (RHS 31B).

*Sepals*.—Arrangement: Outer whorl comprises 3 sepals, one dorsal and two lateral sepals. Overall shape: narrow, elliptical and weakly cupped. Margin: entire and weakly undulate. Length: about 45 mm. Width: about 30 mm. Apex: oval tapering to a point. Texture: Upper and under surface: smooth and satiny. Color (when fully opened): upper surface: white (RHS NN155C). Under surface: white (RHS NN155C) with a haze of green/yellow (RHS 1B) and purple/violet (RHS N81C). with the lateral sepals there is more green/yellow and less purple/violet than with the dorsal sepals.

*Pedicel*.—Length: about 38 mm. Diameter: about 4 mm. Texture: glabrous and smooth. Color: at the raceme from green (RHS 137B) into RHS 138C, into purple/violet (RHS N80D).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 11 mm. Diameter: about 5 mm. Color: white (RHS NN155C).

*Pollinia*.—Quantity: two. Diameter: about 1 mm. Color: orange (RHS N25C).

*Ovary*.—Length: about 4 mm. Diameter: about 5 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Zippity', as illustrated and described herein.

* * * * *